United States Patent [19]
Reed et al.

[11] Patent Number: 5,653,699
[45] Date of Patent: Aug. 5, 1997

[54] SPYROSORBENT WOUND DRESSINGS FOR EXUDATE MANAGEMENT

[75] Inventors: Andrew M. Reed, Arvada; Jon M. Potter, Elizabeth, both of Colo.; Michael Szycher, Lynnfield, Mass.

[73] Assignee: Polymedica Industries, Inc., Golden, Colo.

[21] Appl. No.: 305,273

[22] Filed: Sep. 13, 1994

[51] Int. Cl.$^6$ .................................................. A61F 13/02
[52] U.S. Cl. .................. 604/307; 604/369; 604/370
[58] Field of Search ........................... 604/304, 307, 604/368, 369, 372; 602/41, 44–48, 58, 59

[56] References Cited

U.S. PATENT DOCUMENTS

| | | |
|---|---|---|
| 3,645,835 | 2/1972 | Hodgson . |
| 3,949,742 | 4/1976 | Nowakowski . |
| 3,975,567 | 8/1976 | Lock . |
| 3,978,855 | 9/1976 | McRae et al. . |
| 4,233,969 | 11/1980 | Lock et al. . |
| 4,477,325 | 10/1984 | Osburn . |
| 4,513,739 | 4/1985 | Johns . |
| 4,554,317 | 11/1985 | Behar et al. .......................... 525/28 |
| 4,595,001 | 6/1986 | Potter et al. . |
| 4,657,006 | 4/1987 | Rawlings et al. .................... 604/307 |
| 4,704,130 | 11/1987 | Gilding et al. . |
| 4,747,401 | 5/1988 | Potter et al. . |
| 4,849,458 | 7/1989 | Reed et al. . |
| 4,906,240 | 3/1990 | Reed et al. . |
| 5,098,500 | 3/1992 | Reed et al. . |

*Primary Examiner*—Michael J. Milano
*Attorney, Agent, or Firm*—Olson & Hierl, Ltd.

[57] ABSTRACT

A sheet-form composite suitable as a spyrosorbent wound dressing and exhibiting differential moisture vapor transport rate properties is disclosed. The sheet-form composite includes a hydrophilic, monolithic film layer characterized by having a differential ratio of wet to dry moisture transport rate greater than 1 and a dry moisture transport rate greater than about 2,600 g/m$^2$/24 hrs. This film layer is laminated to a hydrophilic exudate transport layer. The exudate transport layer can itself be, or can further include, a hydrophilic pressure sensitive adhesive applied in a continuous or discontinuous pattern. The sheet-form composite has a moisture vapor transport rate of greater than 2,000 g/m$^2$/24 hrs when dry, and a wet to dry moisture vapor transport rate ratio in the range of about 1.5 to about 10.

20 Claims, 3 Drawing Sheets

SPYROSORBENT WOUND DRESSINGS FOR EXUDATE MANAGEMENT

TECHNICAL FIELD

This invention relates to wound dressings and, in particular, to structures suitable for spyrosorbent wound dressings.

BACKGROUND OF THE INVENTION

A wound produces a mixture of fluids throughout its healing sequence. This fluid is termed exudate. The exudate's biochemical and physical composition is a function of wound type and its position in the healing sequence. Exudate may range from blood and serous fluids to highly viscous proteinaceous liquids. Exudate is beneficial to the wound repair process and contains the cellular and enzymatic materials beneficial to wound healing. The type of wound dictates such parameters as exudate production and speed of healing, etc.

Wounds can be categorized into two broad types: wounds without tissue loss; and wounds with tissue loss.

Wounds without loss of tissue are typically incision wounds formed either as a result of surgery or intro cut.

Wounds which result in the loss of tissue may be the result of trauma or as a secondary event in chronic ailments, e.g., vascular insufficiency, diabetes, etc.

Iatrogenic wounds may also result in the loss of tissue. This is exemplified in such wounds as skin graft donor sites, dermabrasions, etc.

For the purposes of designing a wound dressing, acute and chronic wounds with significant loss of tissue are a challenging area.

Wounds that have significant tissue loss are: dermal ulcers (venous stasis, diabetic and pressure sores), abrasions (traumatic and iatrogenic), donor sites, and burns.

Dermal ulcers are the result of a patient's underlying physical condition. Venous stasis and diabetic ulcers are a direct result of a degeneration of the cardiovascular system. This leads to reduced blood flow in the extremities and subsequent tissue necrosis resulting in the formation of dermal lesions. Pressure sores, or decubitus ulcers, are formed when skin is subjected to unrelenting pressure and abrasion. These factors induce tissue necrosis and ulceration.

Abrasions arise due to trauma, as in the case of "road rash", or from elective procedures such as dermabrasion. These wounds initially produce copious amounts of exudate composed of blood and serous fluid. Traumatic abrasions are frequently contaminated with physical debris which if unattended to will lead to infection.

Donor sites are created by the removal of a thin layer of skin which is utilized as a "skin graft." As in the case of abrasions, donor sites exude blood and serous fluid. These wounds are painful and often require the patient to undergo painkilling treatment.

Burn wounds cover a range of severity, from superficial to full-thickness. Patients suffer fluid loss from their wounds which must be adequately controlled. Severely burnt patients often become immunosuppressed leaving them vulnerable to infection.

Conventionally, wound dressings have been designed and introduced into the market predominantly to absorb the exudate expected from a particular wound. Therefore, a problem arises if a wound dressing which was designed for use on a wound producing a large amount of exudate is used on a wound which produces little exudate. The latter type wound can become desiccated, resulting in a clinically undesirable situation.

The management of exudate, therefore, is of primary concern in making a wound dressing. It has now become an accepted clinical fact that wounds need to remain moist to optimize healing from the standpoint of rate of healing, quality of healing, with minimal or no scarring, etc. As this practice of "moist wound" healing has grown, the need for wound dressings which provide and promote a controlled, moist wound microenvironment has increased.

It is difficult in the clinical environment to choose a dressing having a uniform level of exudate management capability. This decision is compounded by the fact that wounds, during their healing process, can moderate their exudate level. For example, some wounds can produce copious, high levels of exudate during the first few hours or days after injury but subsequently substantially reduce exudate production.

Ideally, modern synthetic wound dressings should also be provided having a structure which allows the dressing to be left on the wound for prolonged periods of time, e.g., about 3 to about 7 days. Therefore, there is a need and desire for a wound dressing capable of accommodating varying degrees of exudate while maintaining a consistent moist wound healing environment.

In particular, differential control of wound exudate is highly desirable if a moist occlusive wound microenvironment is to be maintained. It can be appreciated that if a dressing removes all the exudate that a wound produces, a "dry" wound results and a condition suboptimal for wound healing arises. Similarly, if the dressing does not control the level of exudate sufficiently, then an excess "pool" of exudate can collect which can subsequently leak thus soiling clothing, bed linen, and also breaching any protective barrier to bacterial infection of the wound.

Ideally, a wound dressing also adhesively attaches itself to the wound site. The adhesive utilized must be biocompatible, non-cytotoxic and free of toxic leachable substances, as well as have the desired balance of physical properties such as moisture vapor transport rate, tack, long term adhesion properties, etc. Inasmuch as in use the adhesive will be in direct contact with the wound site and surrounding intact area, it must be physiologically non-toxic and should elicit no more than a minimal allergenic response.

An ideal wound dressing also provides a barrier preventing bacteria from entering the wound through the dressing from the ambient environment while providing the proper moisture vapor transport rate. Other desirable aspects include a dressing's ability to conform to irregular contours of the body, to be self supporting whether wet or dry, and allow passage of gases from the wound. This may be accomplished in part by utilizing elastomeric, flexible, polymeric materials in the construction of the dressing.

Having outlined the major desirable design characteristics of environmental wound dressings it is beneficial to examine the mode of operation of conventional wound dressings to appreciate their deficiencies.

Conventional wound dressings can be categorized into several broad classes: hydrocolloid dressings; film dressings; foam dressings and gel dressings. These dressings maintain specific microenvironments, e.g., moisture, temperature, gaseous transport, etc., around a wound by utilizing a variety of physical mechanisms.

Traditionally, wound dressings have been categorized by determining their capacity to absorb exudate. This has been routinely accomplished by performing laboratory trials in which dressings are immersed in liquids and the quantity of liquid absorbed quantified.

An important clinical property in all occlusive wound dressings is its moisture vapor transmission rate (MVTR), which is the rate at which moisture permeates through the dressing. MVTR is typically measured and expressed in grams per square meter per 24 hour day ($g/m^2/24$ hrs). A conventional dressing has a fixed MVTR regardless of exudate level.

More recently, a new class of environmental wound dressings, "spyrosorbent dressings", have been created. The term "spyrosorbent" is defined as breathable absorbent. Unlike conventional wound dressings, a spyrosorbent dressing has a differential MVTR capability. Spyrosorbent wound dressings not only manage exudate by absorption but have the ability to adjust their moisture vapor transport properties in response to the level of exudate available. That is to say, spyrosorbent dressings possess a level of active intelligence due to their physical and chemical structure.

Conventional dressings also differ markedly from one another in their attributes, such as conformability, adhesiveness, and ease of use. They also differ dramatically in the mechanisms by which they seek to manage exudate.

Film dressings are typically relatively thin films, which utilize exclusively the moisture vapor transport properties of the film materials from which they are constructed. Film dressings are conformable, but on moderately to highly exuding wounds the exudate tends to collect under such film dressings and form "pools". This collection of exudate indicates that the MVTR of conventional polymer film dressings is too low to handle the exudate from many wounds. It has also been suggested that the "pool" of exudate may increase the risk of bacterial proliferation leading to infection. Similarly, if the "pool" reaches excessive proportions, leakage will occur, thus breaking the bacterial barrier. The thin film category of dressings has also shown, however, that by suitable choice of film thickness and molecular structure of the film, MVTR can be substantially increased or reduced dependent upon the requirements of the dressing.

Hydrocolloid and gel dressings all utilize absolute absorption mechanisms by which to manage exudate. As a result of this absorption, they generally tend to be relatively thicker dressings, and less conformable than the film dressings. This can cause a series of problems when utilized in a clinical environment. For example, the ability for moisture to pass through the dressing to the external environment is minimal. On highly exuding wounds, the dressing's absorption capacity can be exceeded leading to leakage and subsequent disruption of the bacterial barrier. Some hydrocolloid compositions can dissolve and enter into the wound bed itself, thus requiring time consuming cleaning, which disrupts the wound site, at subsequent dressing changes.

Alginate dressings, a subset of gel dressings composed of alginate, are examples of dressings which are sometimes supplied as dehydrated or partially hydrated structures. On application to the wound and subsequent absorption of exudate such dressings undergo gelation. However, the swelling of the dressing results in the dressing structure moving away from the wound bed and providing potential air spaces and pockets in which bacteria may proliferate. Moreover, dressings which are supplied in a partially hydrated state are not supplied with a pressure sensitive adhesive coating. Further taping or application of a secondary dressing is therefore required to assure adequate attachment.

Alginate dressings are supplied as a dry, fibrous, mat structure. Alginate dressings are capable of absorbing large quantities of exudate. During absorption they undergo a gelation reaction due to the interchange of sodium and calcium ions between the exudate in the wound bed and the alginate material in the dressing. Alginate dressings, like other gel dressings, require the use of secondary dressings to secure them.

Gel dressings are generally water or saline hydratable or swellable gel (hydrogel) materials supplied on a moisture impermeable polymeric backing sheet. The backing sheet prevents the hydrogel from dehydrating and desiccating the underlying wound. These gel materials have little or no vapor transport capacity. In some instances, it is recommended that the impermeable backing sheet of the gel dressing be removed during the healing sequence, especially on heavily exuding wounds. The removal of the sheet encourages the dehydration of the hydrogel. This, in turn, increases the dressing's ability to handle high levels of exudate. During the dehydration, however, the gel dressing becomes noncompliant, resulting in damage to the underlying wound.

Gel wound dressings, in general, do not dissolve and contaminate the wound and, when hydrated, are more conformable than hydrocolloid dressings but less conformable than thin film dressings.

Foam type dressings utilize both a moisture vapor transport and absorption mechanism by which to manage exudate. These dressings, due to their chemical nature and high degree of hydrophilicity, however, tend to swell and lose mechanical integrity when wet.

Foam dressings manage exudate by evaporation of the aqueous portion of the exudate through the dressing to the surrounding environment. The control of MVTR is a function of the chemical composition of the foam coupled with the pore structure. Due to the gross pore sizes of conventional foams, however, foam dressings tend to desiccate wounds resulting in dressings which become brittle and non-conformable during use. These hardened dressings often traumatize the underlying healing wound bed. In addition, either special processing or a wetting agent, or both, are required to make the foam hydrophilic.

Dependent upon the type of foam structure used, exudate can also be managed by capillary action into the pores of the structure. Most conventional foam materials used as dressings contain interconnecting pores and thus provide limited bacterial barrier properties because the mean pore diameter exceeds the dimensions of many bacteria. Similarly, such dressings contain pore sizes which are sufficiently large as to fall into the range of sizes into which regenerating tissue will grow. As a result, ingrowth of tissue into the dressing's structure occurs thus impeding removal of the dressing and traumatizing the wound site.

Some attempts have been made in the past to overcome the foregoing deficiencies of film dressings and, in particular, the "pooling" of wound exudate.

Polymer film dressings as described in U.S. Pat. No. 3,645,835 to Hodgson and. U.S. Pat. No. 4,513,739 to Johns are thin and possess high conformability. The wound contacting surfaces are coated with pressure sensitive adhesives carried on the film. The films that are used are liquid impermeable poly urethane elastomers. Thus wound exudate cannot enter into the film. The sole mode of exudate control is by allowing the vapor of the aqueous portion of the exudate to permeate into the polymer film from where it diffuses into the external environment. As the moisture vapor permeability is low, however, the polymer film's absolute absorption capacity is also low, especially when compared to hydrocolloid dressings.

In U.S. Pat. No. 4,747,401 and U.S. Pat. No. 4,595,001, both to Potter et al., a surgical wound dressing is described composed of a continuous hydrophilic film laminated to a discontinuous adhesive layer. The film is selected to have a higher moisture vapor permeability when it is in contact with water than with moisture vapor. The moisture vapor permeability of the laminate dressing is stated to be not more than 2000 g/m$^2$/24 hrs when the adhesive layer is in contact with water vapor but not liquid water, and not less than 2,500 g/m$^2$/24 hrs when the adhesive layer is in contact with liquid water. However, a MVTR of not more than 2,000 g/m$^2$/24 hrs is undesirably low for the management of moderate to heavy exudate. Moreover, the chemical and laminate composition of the polymer films described structurally restricts the degree of differential MVTR which might be attainable with such a dressing structure. Thus, spyrosorbent wound dressings which simultaneously balance moisture vapor transport and absorption mechanisms within one dressing are desirable and needed. In particular, an ideal spyrosorbent dressing would have a low profile, be highly conformable, breathable and absorptive and not become exhausted or have a finite exudate management capacity.

This need has been satisfied in part by the wound dressings described in U.S. Pat. No. 4,906,240 and U.S. Pat. No. 5,098,500, both to Reed, et al., owned by the assignee of the present invention. The disclosures of the foregoing patents are incorporated herein by reference. Sheet-form wound dressings are described which comprise a porous sheet of absorbent elastomeric segmented polyurethane having an open pore size gradient, such that larger pores are away from the wound side, and an apertured adhesive facing contiguous with the large pore surface. This apertured adhesive structure enhances the management of exudate by providing fluid channels for capillary transport of proteinaceous exudate to the interior of the porous sheets. By varying the chemical composition of the film layer, the MVTR of the film and, thus of the wound dressing, can be adjusted as desired.

One spyrosorbent environmental membrane laminate dressing has been developed and sold under the trademark, MITRAFLEX® by PolyMedica industries, Inc. (Golden, Colo.), the assignee of this invention. Briefly described, this dressing is a trilaminate structure of porous, pressure sensitive adhesive attached to an absorptive, polyurethane, microporous membrane which is laminated to a thin, transparent, hydrophilic, polyurethane film. This spyrosorbent wound dressing is used to manage exudate from dermal ulcers, skin donor sites, superficial burns, abrasions and lacerations.

A description of the development and properties of the MITRAFLEX® dressing can be found in the article by Reed, Andrew M., "Mitraflex: Development of an intelligent Spyrosorbent Wound Dressing," *Journal of Biomaterials Applications* 6: 3–41, Technomic Publishing Co., Inc. (1991).

The spyrosorbent wound dressings of the present invention further satisfy the ongoing need for exudate management by providing dressing structures having differential MVTR properties and improved exudate management capability. Such structures desirably adjust a dressing's exudate transport away from the wound site in response to the quantity of exudate produced by a wound and modulate the rate of exudate transport.

SUMMARY OF THE INVENTION

The present invention contemplates sheet-form composites suitable for spyrosorbent wound dressings. The term "spyrosorbent" as applied to wound dressings herein refers to wound dressings which enhance the healing of a wound by providing around the wound a microenvironment which promotes healing by modifying and self-adjusting the moisture vapor transport rate (MVTR) of the dressing in response to the level of exudate produced by the wound.

More particularly, a preferred spyrosorbent dressing is a laminate structure having a MVTR greater than 2,000 g/m$^2$/24 hrs when dry and comprising: (1) a relatively thin film layer of continuous, monolithic, hydrophilic material which possesses a differential MVTR property; and (2) at least one exudate transport layer contiguous with all or a portion of the film layer. The differential wet-to-dry MVTR ratio for the spyrosorbent dressing is at least about 1.5. In use the exudate transport layer is applied in contact with the wound.

Spyrosorbent dressing structures contemplated herein possess an absorption mechanism and breathability mechanism which allows for exudate management to be controlled by the combined effects of absorption and evaporation. The film layer is a monolithic, microporous hydrophilic polymer, preferably less than about 5 mils (about 125 microns) in thickness, when dry.

The film layer used in the dressings of the present invention possesses the property of having a differential MVTR between "wet" and "dry" states. The term "differential" means that in a fully hydrated (wet) condition the polymeric film possesses a wet MVTR which is significantly greater than that exhibited by the same film when it is only partially or totally dehydrated (dry). The differential wet to dry MVTR ratio for the film is greater than 1, and preferably is at least about 3:1. The MVTR of the film in its dry state is at least about 2,600 g/m$^2$/24 hrs. The ability of the film to adjust its MVTR allows the overall dressing structure to self-adjust and increase its overall MVTR to manage levels of exudate in highly exuding wounds, then reduce its MVTR when the wound no longer produces copious exudate. Thus with a single wound dressing, varying exudate levels can be controlled and managed, and a balanced and desirable optimal moist wound healing environment can be maintained.

The exudate transport layer is constituted by physiologically tolerable material that is hydrophilic and is hydratable or swellable by, but not soluble in, the wound exudate. The exudate transport layer can be comprised of one or more of the following absorptive materials: hydrocolloids, gels (hydrogels or hydroalcoholic gels), foams, textiles (woven or nonwoven), membranes (microporous or macroporous) and hydrophilic adhesives (pressure-sensitive or bioadhesive). Optionally, a releasable liner layer can be attached to the external face of the exudate transport layer. Also contemplated are plural such exudate layers constituted by different materials selected from the foregoing grouping.

The spyrosorbent dressings of the present invention maintain a desired level of moisture, temperature and vapor exchange at the wound site. By the control of these properties, the microenvironment thus produced optimizes wound healing conditions. At the same time, the spyrosorbent dressings of the present invention manage exudate, are biocompatible, non-toxic, and conformable, and provide a barrier against bacterial contamination as well.

The disclosed spyrosorbent dressings incorporate the ability to adjust its MVTR according to the degree of exudate production of the wound thus providing a level of "interaction" or "intelligence" between the dressing and wound. Thus, the spyrosorbent wound dressings of the present invention advantageously control exudate and moisture level at the wound site by controlling the overall absorption and moisture vapor transport rate of the exudate. These parameters can be adjusted by appropriately balancing the absorbent property of the material or materials for the exudate transport layer to the film layer, and by the chemical composition of the film layer as described herein. Thus a series of wound dressings which provide a continuum of different microenvironments can be readily provided. These dressings can be designed to suit particular wound types, e.g., ulcers, skin donor sites, burns, high exuding and low exuding wounds, etc.

The beneficial ability of spyrosorbent dressings to accommodate a wide range of exudate levels over protracted periods of time while maintaining a moist healing environment makes these dressings clinically superior to those currently available. Because the dressings possess a level of interaction, or "intelligence", they can thus monitor and manage levels of exudate without the intervention of clinical staff. As a result, these wound dressings can be utilized unattended over extended periods of time, thereby providing considerable cost savings in the treatment of a wide range of dermal lesions.

Other benefits that flow from the disclosed spyrosorbent dressings are ease of use and continued ability to maintain the desired microenvironment for optimal wound healing.

Numerous other advantages and features of the present invention will become readily apparent from the following detailed description of the invention, the accompanying examples, the drawings, and the appended claims.

DETAILED DESCRIPTION OF THE PREFERRED EMBODIMENTS

While this invention is susceptible to embodiment in many different forms, preferred embodiments of the invention are shown and described in this specification. It should be understood, however, that the present disclosure is to be considered as an exemplification of the principles of this invention and is not intended to limit the invention to the embodiments illustrated.

Figure 1:
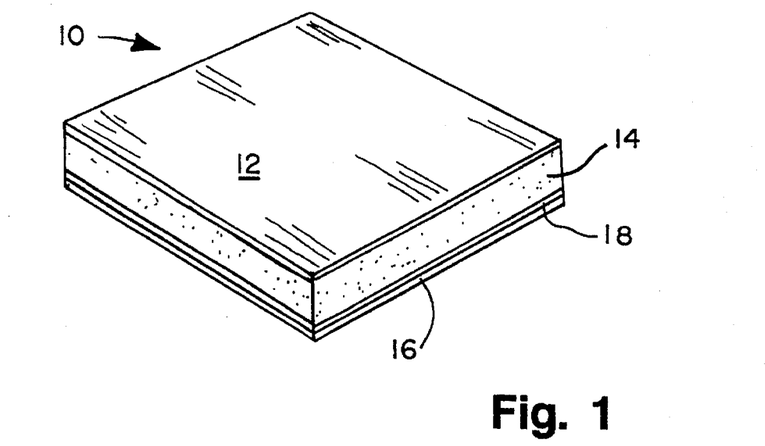
FIG. 1 is a perspective view of a spyrosorbent dressing embodiment of the present invention.

As shown in FIG. 1, a wound dressing 10 of the present invention includes a continuous, monolithic, hydrophilic film layer 12 contiguous with a discrete, hydrophilic, absorptive exudate transport layer 14. The terms "continuous" and "monolithic" as used herein mean that the film material, while vapor permeable, is a unitary structure and contains no discontinuities visible to the naked eye. Optionally, a releasable liner 16 can be attached to adhesive layer 18 which is coextensive with exudate transport layer 14.

Figure 2:
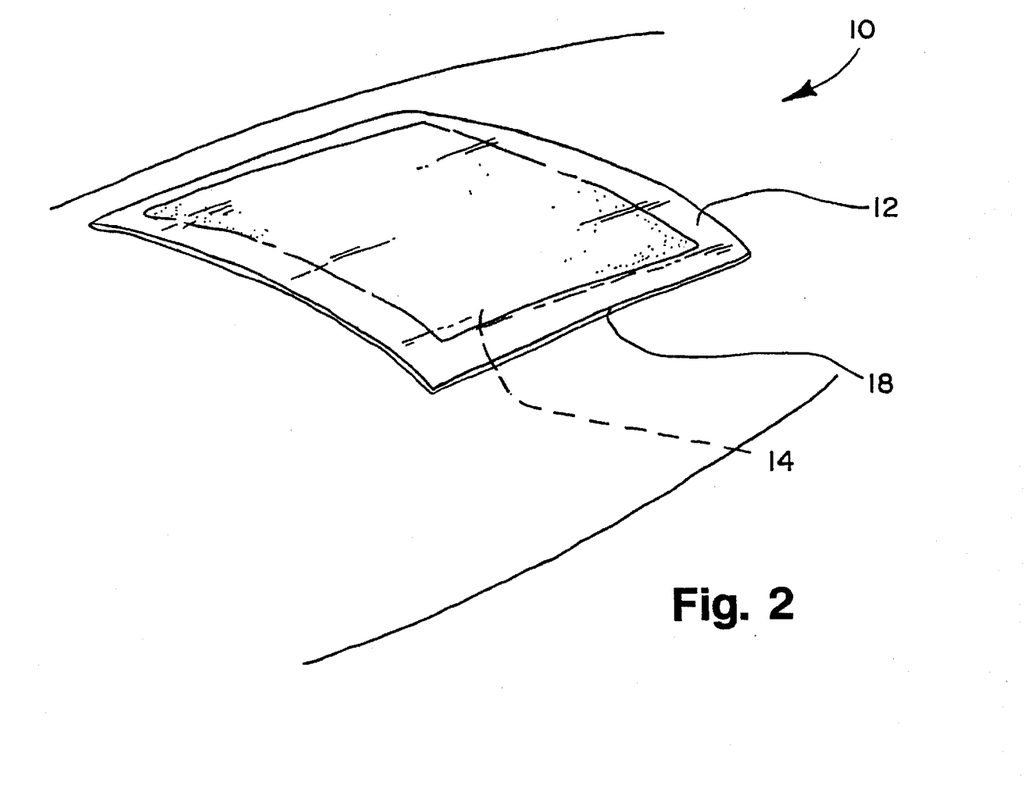
FIG. 2 is a perspective view illustrating another spyrosorbent dressing embodiment of the present invention as applied to a wound site.

Alternatively, as shown by the embodiment in FIG. 2, the exudate transport layer 14 can be contiguous with a portion of transparent film layer 12 so as to form an "island" under the film. In this particular embodiment, the peripheral or border portion of the film layer which extends beyond the island can contact the skin of the patient beyond the wound site for securement of the dressing. A physiologically tolerable, biocompatible, hydrophilic adhesive layer 18 which is pressure sensitive can be included in at least the border portion but can also be substantially coextensive with the exudate transport layer. The term "biocompatible" as used herein refers to a material that is relatively non-thrombogenic and non-irritating when used in direct contact with blood and with tissue.

Unless otherwise indicated, the MVTR of the materials or dressing were determined by a modified ASTM E-96 method. A description of the ASTM E-96 method can be found in "Standard Test Methods For Water Vapor Transmission Of Materials.", *Annual Book Of ASTM Standards*, 15.09, pp 833–842, (1986).

In the modified ASTM E-96 Test, a circular dressing sample of about 3 inches (about 7.5 cm) diameter is sealed with the bottom or wound contacting side against the open mouth of an aluminum "test cup" containing about 10 to about 20 milliliters of distilled water and weighed. This cup assembly is then placed in a dry incubator with an air flow and a controlled ambient temperature set at about 37° C. (about 98.6° F.) for about 24 hours. MVTR was determined by periodically manually weighing the cup to measure the amount of water lost over time. The test cups were placed upright to expose the dressing to low moisture contact (i.e., 100% relative humidity water vapor) and inverted to expose the dressing to high moisture contact (i.e., in direct contact with liquid water).

The bottom or wound-contacting side of each of the dressing samples, was separately exposed to both low moisture contact and to high moisture contact, and the value obtained from each test recorded as "dry" MVTR and "wet" MVTR respectively.

The ratio of the value obtained for wet MVTR to that of dry MVTR for the sheet-form composite is an important factor in producing a dressing which can self-adjust and accommodate the varying levels of absolute exudate production. It was found that a desirable ratio preferably lies in the range of from about 1.5 to about 10, more preferably from about 2.5 to about 5.5. It may readily be appreciated that this ratio is related to the combined effects of moisture transport rate through the exudate transport layer and the ability of the polymeric film contiguous therewith in the dressing structures to cycle between "low" and "high" (or vice versa) MVTRs and thus manage "low" to "high" (or vice versa) exudate levels.

As well as having a desirable wet to dry MVTR ratio, the absolute moisture vapor transport of the dressing's material is an important factor in providing an occlusive spyrosorbent dressing with broad clinical utility. It has been found that the minimum dry MVTR of the dressing is greater than 2,000 $g/m^2/24$ hrs, preferably about 2,200 $g/m^2/24$ hrs to about 2,600 $g/m^2/24$ hrs, regardless of ambient temperature, to provide widely applicable, clinically superior spyrosorbent dressings of this invention.

Thus, two parameters: the ratio of wet to dry MVTR and the dry MVTR, can be used to delineate a range or area within which the spyrosorbent dressings of the current invention preferably operate. This range is diagrammatically represented in FIG. 3 for illustrative embodiments of the present invention.

Figure 3:
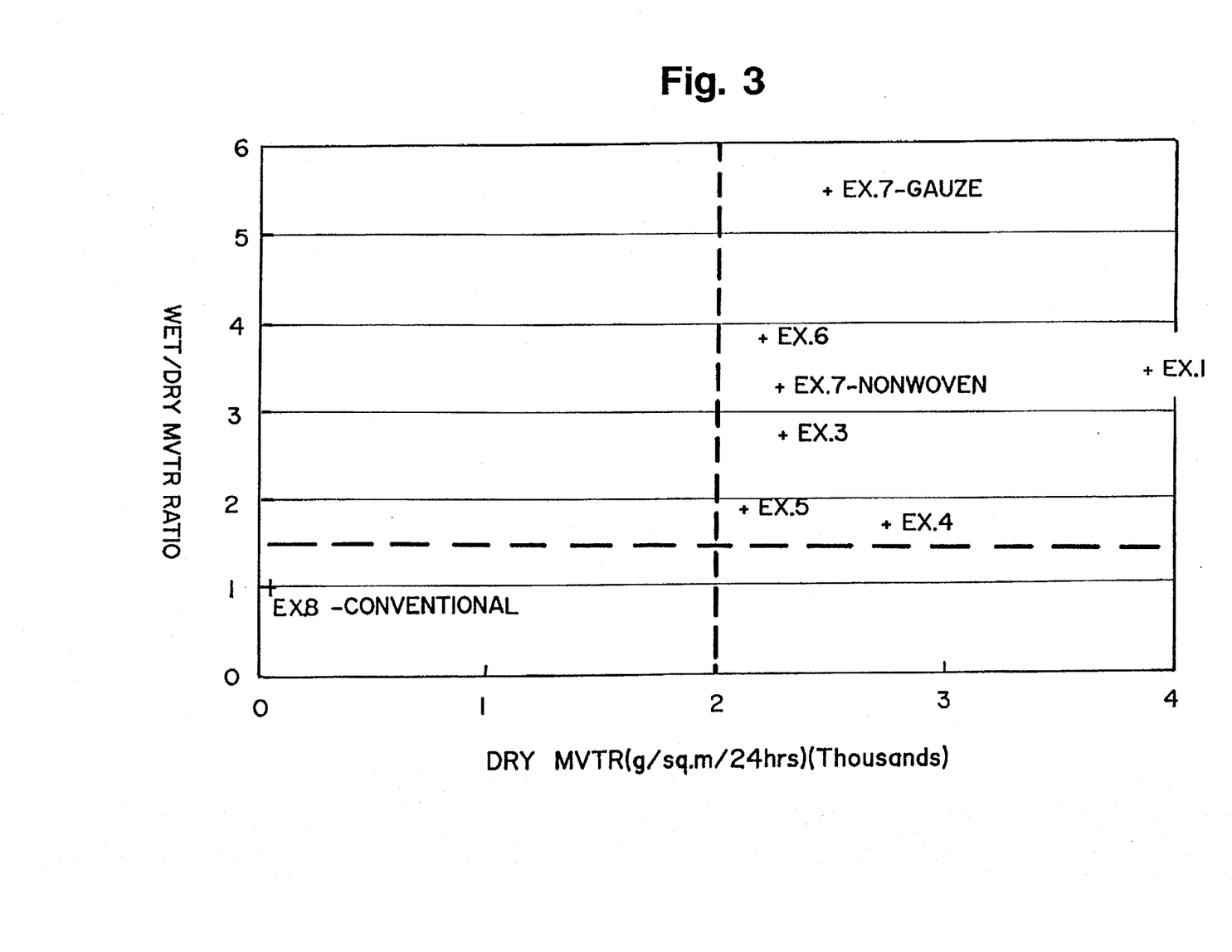
FIG. 3 is a graphic representation of the ratio of wet to dry moisture vapor transport rate as a function of the dry moisture vapor transport rate of spyrosorbent wound dressings embodying the principles of this invention.

In FIG. 3, the calculated average wet to dry MVTR ratio is plotted as a function of the average dry MVTR value for each of the spyrosorbent structures described in Examples 1, and 3–7, below. For comparison purposes, the fixed ratio of the wet to dry MVTR values obtained for the non-spyrosorbent wound dressing described in Example 8 is also shown. Each of the described composite structures embodying the present invention possesses an average dry MVTR of greater than about 2000 $g/m^2/24$ hrs and a wet to dry MVTR ratio of at least about 1.5.

The dashed boundary line in FIG. 3 clearly illustrates the performance capabilities of the present dressings. In contrast, the sorbency of the dressings described by Potter et al. in U.S. Pat. No. 4,774,401 and U.S. Pat. No. 4,595,001 reportedly have a dry MVTR of 1100 to 1800 $g/m^2/24$ hrs when exposed to water vapor which dry MVTR value is considerably below that of the spyrosorbent dressings disclosed herein.

In the dressing structures of the present invention, the exudate transport layer can be applied to be either in contact with the entire surface of the film layer or alternately to be present as an island on a portion of the film layer as illustrated in FIGS. 1 and respectively. If pressure sensitive adhesive is applied, it is preferably applied in a discontinuous fashion such as a printed pattern.

The dressing structures described can also have the wound contacting side of the exudate transport layer affixed to a suitable protective release liner system, such as siliconized paper. These dressing structures also can be cut to the desired shape and size and packaged in suitable sterilizable pouches. The dressing structures can be sterilized by an appropriate method, such as gamma irradiation, ethylene oxide sterilization, steam, or the like, prior to use as a wound dressing.

The film layer of the wound dressings of the present invention is a hydrophilic, moisture vapor permeable film having a relatively high MVTR wet as well as dry, and having a differential wet-to-dry MVTR ratio that is greater than 1, preferably at least about 3:1. The dry MVTR of the hydrophilic film is greater than about 2,600 $g/m^2/24$ hrs, preferably about 3,000 to about 4,000 $g/m^2/24$ hrs. In particular, the film layer is preferably a continuous, monolithic, hydrophilic polymer. A particularly preferred film layer is made from a segmented polyurethane which can be cast as a thin, continuous, monolithic film of desired thickness from a solvent and which is liquid impermeable but water vapor permeable.

Such polyurethanes are described in U.S. Pat. No. 4,849,458 ('458 Patent) to Reed et al., assigned to the assignee of the present invention, the disclosure of which are incorporated herein by reference. To appreciate fully the usefulness of these polyurethane based films, a brief discussion of their properties and mode of action is warranted.

The polyurethanes disclosed in the '458 Patent are hydrophilic, segmented polyether polyurethane-urea resins (hereafter referred to as polyetherurethanes) based on polytetramethylene glycol and polyethylene glycol polyols. These materials exhibit an increase in tensile strength and elongation when wet with water, exhibit an MVTR several orders of magnitude higher than that of silicone derived films and are capable of forming visually clear films. The hydrophilicity and hence the MVTR, of these polyetherurethanes can be controlled either intrinsically by varying the composition and ratio of the segments or extrinsically by incorporating hydrophilic polymers or wetting agents which are soluble in the segmented polyetherurethane resin, or both.

By adjusting the stoichiometric quantities of the aforementioned glycols it has been possible to manufacture a range of polyetherurethanes which exhibit predictable mechanical properties in both dry and wet states. Similarly, a series of materials can be synthesized with varying moisture vapor transport rates. By increasing the polyethylene glycol concentration in these formulations, it has been found that increases in moisture vapor transport rate may be accomplished.

While not wishing to be bound by a particular theory, it is believed that the polymers of the '458 Patent behave as follows. Water, being a small, highly polar molecule, is known to participate in "bridging" reactions with various chemical groupings through its hydrogen atom. In the case of the segmented polyetherurethane resins of the '458 Patent, the hydrogen atoms in the water molecules participate in a "bridging" reaction between oxygen atoms in the polyether "soft" block segments. The "soft" blocks are considered to be coiled and the hydrogen "bridging" takes place both between oxygen contained in adjacent loops of the mixed polyether coil and between oxygen present in other surrounding coils (either in the same polymer chain or a second chain). The "bridging" increases the strength of the respective chain which is observed as an increase in mechanical strength of the polymer.

Similarly, the presence in the foregoing segmented polyetherurethane of the urethane and urea bonds makes a secondary level of molecular interaction possible. These interactions are due to the association of the various electrically charged species present along the backbone of the polymer. These short range interactions have a high degree of "hydrogen bond" character, and are often referred to as virtual or pseudo cross-links.

These interactions take place both within and between polymer chains. By adjusting the quantity and type of chemical groupings in the polymer chain, it is possible to manipulate the level of virtual cross-linking within the molecule. This allows a level of control over the conformation of the polymer when in the bulk phase.

Virtual cross-linking may be enhanced by the presence of hydrogen bonding molecules such as water. Water assisted virtually cross-linked polyetherurethanes can be prepared. These polyetherurethanes become stronger when hydrated or saturated with hydrogen bonding liquids. Virtual cross-links are approximately ¹⁄₂₀th of the normal covalent bond strength, and may be formed and broken an infinite number of times. This ability to be formed and broken provides strong conformable polymers with high flex lives.

The density of virtual cross-links and their positioning in the polyetherurethane chain used to manufacture the polymeric film of the present invention has been designed to facilitate the desired degree of virtual cross-linking so as to enable the molecules to attain a coiled conformation. The formation and retention of the coil conformation is assisted by the presence of hydrogen bonding materials such as water. Virtual cross-linking may be controlled by factors such as the type of polyurethane extension agent, the type, the molecular weight, and stoichiometry of the macroglycols used in the synthesis of the polymer.

The proposed polyetherurethane conformation is such that when equilibrated with a hydrogen bonding liquid such as water, a molecular bridging reaction occurs. When fully hydrated, the polyetherurethane adopts a coiled conformation. The coils maintain their conformation by the bridging reaction of the water molecules. The presence of the coiled molecules in the film allows small charged molecules such as water, to pass through the center of the coil thus passing through the film at an increased rate. On dehydration of this structure, the coils partially collapse. The collapse of the coils hinders the movement of water molecules through the film.

The practical yet surprising outcome of the change in conformation between the hydrated and non hydrated states of the foregoing segmented polyetherurethanes is that their wet and dry films exhibit a differential MVTR. In particular, their films have wet MVTR values that are significantly greater than their dry MVTR values. It has also been found that this differential MVTR property is observed even when isotonic saline solution is used instead of water for determining MVTR values.

A differential MVTR is useful in monitoring whether a wound is highly exuding or only minimally exudating. Such a mechanism provides for a wound dressing which, when placed on a highly exuding wound, can accordingly increase its MVTR to manage the increased amount of exudate. As the healing process progresses and the wound produces lower quantities of exudate, the wound dressing in response to the reduced level of exudate production becomes less hydrated and also reduces its MVTR. As well as being permeable to moisture vapor, this polymeric film layer is permeable to gases, such as $CO_2$ and $O_2$. It will be readily appreciated that due to the film's monolithic characteristics, the film material is impermeable to liquids or bacteria.

Figure 4:
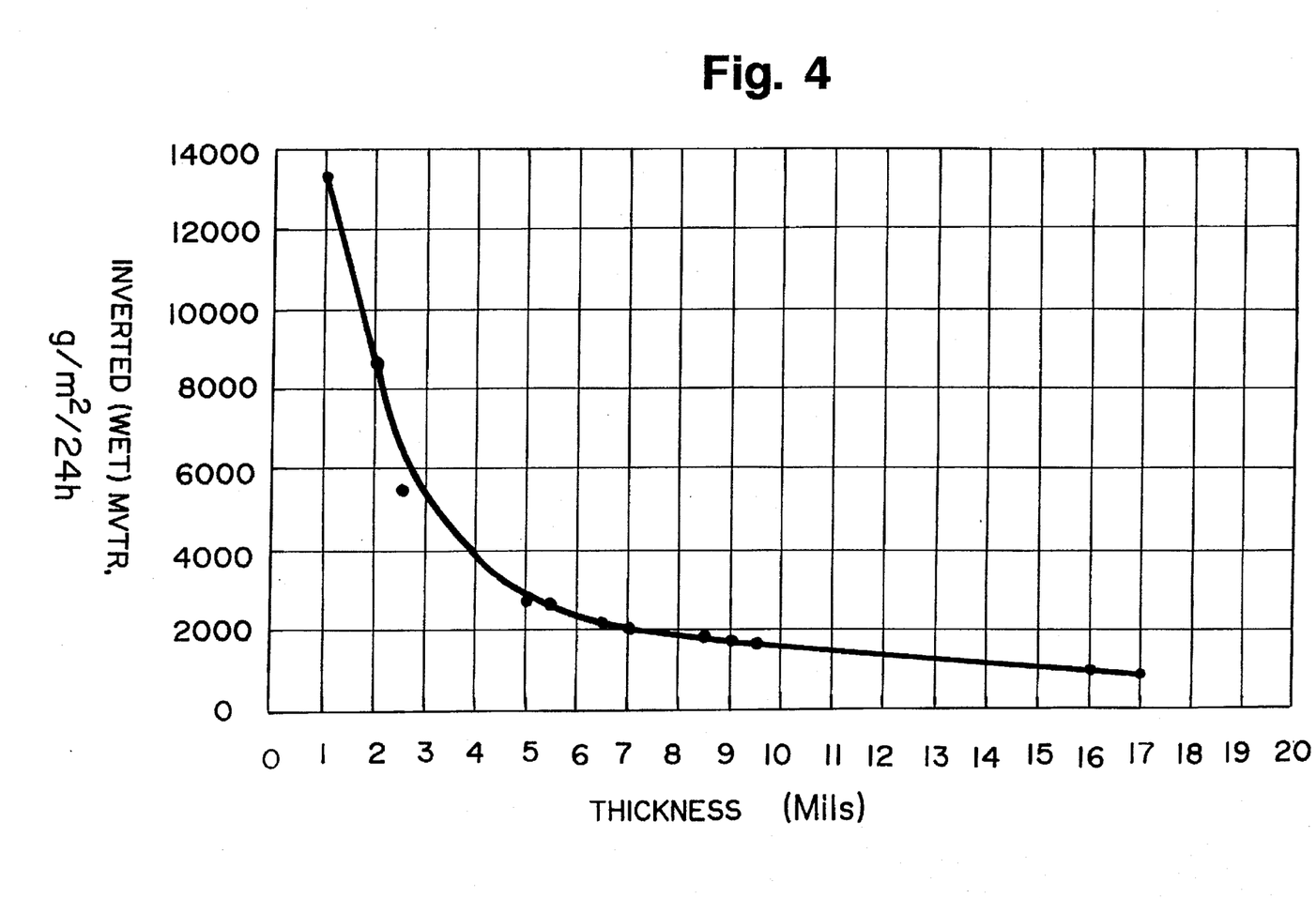
FIG. 4 is a graphic representation of the dry moisture vapor transport rate of a spyrosorbent polymeric film embodiment plotted as a function of film thickness.

The thickness of the polymeric film is also a factor in obtaining a desired wet MVTR. This is graphically illustrated in FIG. 4 where the wet MVTR of a segmented polyetherurethane polymer film is plotted against a film thickness ranging from about 1 mil (about 25 microns) to about 17 mil (about 425 microns). A wet MVTR of about 6,000 g/m$^2$/24 hrs was achieved at a film thickness of about 2.5 mil (about 62.5 microns). While a thickness of greater than 3 mil can be used, e.g., 5 mil (125 microns) no further advantage in MVTR is to be expected. Thus, for the present purposes the film thickness more preferably is about 3 mil (about 75 microns) or less, and most preferably about 1 mil (about 25 microns) to about 1.5 mil (about 37.5 microns).

Useful materials for the film layer include but are not limited to the following segmented polyetherurethane-urea resins available commercially under the designation MITRATHANE® from PolyMedica Industries, Inc. (Golden, Colo.).

MITRATHANE® M1020 is a segmented polyetherurethane-urea derived from diphenylmethane diisocyanate, polytetramethylene glycol having a number average molecular weight of about 1,000, and organic amines in an amount sufficient to provide for about 20-fold chain extension;

MITRATHANE® M2007 is a segmented polyetherurethane-urea derived from diphenylmethane diisocyanate, polytetramethylene glycol having a number average molecular weight of about 2,000, and organic amines in an amount sufficient to provide for about 7-fold chain extension; and MITRATHANE® MPU-5 is a segmented polyetherurethane-urea derived from diphenylmethane diisocyanate, polytetramethylene glycol, polyethylene glycol, and organic amines as chain extenders.

The exudate transport layer of the dressing is affixed to one surface of the film layer and preferably has an absorptive capacity for transporting exudate to the film. Thus, a spyrosorbent wound dressing embodying the principles of this invention can balance its MVTR in response to the level of exudate. In one embodiment aspect, at relatively lower exudate levels, the rate limiting layer is primarily the exudate transport layer since it is closest to the wound. At relatively higher exudate levels, however, the film layer, which is furthest from the wound, further balances the MVTR by virtue of its differential MVTR property in response. Thus, in effect, changes reflected in the exudate transport layer due to increased or decreased exudate levels in turn are balanced by the film layer which modulates the overall sorbent property of the dressing structure accordingly. Thus, the microenvironment around the wound is controlled making wound management substantially self-monitoring.

Exemplary hydrophilic materials for the exudate transport layer can include hydrocolloids, gels, foams, textiles, membranes, pressure sensitive adhesives and combinations thereof without limitation so long as the material is physiologically tolerable and clinically acceptable.

Suitable hydrocolloids include, but are not limited to, natural gums, such as plant exudates (gum arabic, ghatti, karaya, and tragacanth); plant seed gums (guar, locust bean and acacia), seaweed extracts (agar, algin, alginate salts and carrageenin), cereal gums (starches and modified starches), fermentation or microbial gums (dextran and xanthan gum), modified celluloses (hydroxymethylcellulose, microcrystalline cellulose and carboxymethylcellulose, microcrystalline cellulose and carboxymethylcellulose) pectin, gelatin, casein and synthetic gums (polyvinylpyrrolidone, low methoxyl pectin, propyleneglycol alginates, carboxymethyl locust bean gum and carboxymethyl guar gum) and like water-swellable or hydratable hydrocolloids.

Exemplary gels include, but are not limited to, gels comprising a hydrophilic lattice of long-chain polymers containing from about 1% to about 99% water (referred to as hydrogels) and hydroalcoholic gels thereof. The polymers can be cross-linkable polymers of polyacrylamide and polymethacrylic acid, which preferably are swellable by, but not soluble in, the water present in wound exudate to form a viscous gel-like dispersion.

Suitable hydrophilic polymer materials are polyacrylic acid allylsucrose copolymers and salts thereof. The so-called carbomers, for example, are the homopolymers of acrylic acid crosslinked with an allylether of pentaerythritol, an allylether of sucrose or an allylether of propylene and are sold in varying viscosities and molecular weights under the trademark CARBOPOL by B.F. Goodrich Company (Cleveland, Ohio). Also useful are non-drying, aqueous jellies of glycerol polyacrylate sold under the trademark HISPAGEL in varying viscosities by Hispano Quimica S.A. (Barcelona, Spain), and gels of radiation crosslinked hydrophilic polyoxyethylene described in U.S. Pat. No. 3,419,006 to King and sold under the Trademark VIGILON by C.R. Bard, Inc. (Murray Hill, N.J.).

As a subset of gels, alginates are a special variation supplied as a fibrous material manufactured from varieties of plants, especially extracts of kelp or seaweed. Sodium alginate produce viscous liquids and calcium alginate forms gels. Consequently sodium and calcium salt can be blended to achieve the desired level of gelation. Alginates are typically available in substantially dehydrated form and swell upon absorption of wound exudate.

Useful membrane structures preferably have a microporous as well as a macroporous structure. Exemplary membrane structures include elastomeric polymers having controlled pore sizes prepared from the segmented polyetherurethane-urea family of polymers sold under the trademark MITRATHANE by PolyMedica Industries, Inc. (Golden, Colo.). A description of the properties and preparation of these polymers can be found in U.S. Pat. No. 4,704,130 to Gilding et al. and U.S. Pat. No. 3,635,907 to Schulze et al., the disclosures of which are incorporated herein by reference. Other such spandex type polymers which can be used are available under the designations LYCRA® from G.I. DuPont de Nemours, PELLETHANE® from Dow Chemical Co. and ESTANE from B.F. Goodrich Co.

Exemplary foams include, but are not limited to, hydrophilic polyester polyurethanes and polyetherurethanes of open or closed cell foam type. Description of modified open cell foams can be found in U.S. Pat. No. 3,975,567 to Lock and in U.S. Pat. No. 3,978,855 to McRae. The relevant disclosure of each is incorporated herein by reference. These foams have been physically modified to change either their absorbency or reticulation properties.

Exemplary textiles include textiles that can be woven as well as nonwoven, of natural or synthetic fibers or blends thereof. These can be cellulosic such as cotton lint, cotton gauze, cotton wool pads, cotton and rayon wool pads, linen cloth and the like. Cotton gauze, in particular, is typically used in hospitals and doctors' offices, is defined in the U.S. Pharmacopeia, and is well known in the art. Synthetic nonwoven textiles include, but are not limited to, polyester including spun bonded polyester, polypropylene including melt blown polypropylene, microporous films of plasticized polyvinyl chloride, composites of synthetic films with natural fibers and like commercially available materials. A number of other non-woven textiles suitable for use in dressings are well known in the art.

The film layer is preferably laminated to the exudate transport layer by either application of heat or pressure, or both, or by a suitable adhesive. In some instances, exudate transport layers of hydrocolloids or gels can exhibit adhesive properties in conjunction with their absorption capability. Alternatively, the exudate transport layer itself can be a hydrophilic adhesive, preferably be pressure sensitive, or of a material possessing bioadhesive properties. Where the exudate transport layer is a pressure sensitive adhesive, and is applied as by a printing technique in a defined pattern with open spacing, only minimal absorptive capacity is achieved. The adhesive properties of the dressing afford a method whereby the dressing can be attached to the intact skin surrounding a wound site. Alternatively, an adhesive layer can be contiguous with the film layer.

Adhesives can be formed from polymers containing hydrophilic groups, such as hydroxyl, carboxyl, amine, amide, ether and alkoxy, so long as the resulting adhesive is not soluble in the exudate, and remains noncytoxic and substantially nonallergenic to the patient.

Preferably, the adhesive is a visco-elastic, acrylic-based pressure sensitive adhesive which is cohesive and inherently tacky in its normal dry state, and is capable of forming a lamina with the film layer or exudate transport layer under heat or pressure. Exemplary materials used as adhesives include blends of vinyl ether or acrylic polymers, with or without added tackifying resins. One preferred acrylic-based adhesive is a copolymer of 2-ethylhexyl acrylate and about 10 to about 25 mol percent acrylic acid. A description of this adhesive can be found in U.S. Pat. No. 4,906,240 to Reed et al., incorporated herein by reference.

The adhesive can be applied to the film layer or to the exudate transfer layer by known techniques as a hot melt, by a transfer print process, or the like expedients. A transfer print process is preferred. Alternatively, the adhesive can be applied to a suitable release liner first and the adhesive coated surface of the liner applied to all or a portion of the wound contacting layer of the wound dressing, and removing the liner thereafter.

Water-swellable, but water-insoluble, fibrous cross-linked carboxy-functional polymers suitable as bioadhesives are described in U.S. Pat. No. 4,615,697 to Robinson, the relevant disclosures of which are incorporated herein by reference. One preferred bioadhesive is a polyacrylic acid cross-linked with divinyl glycol commercially sold under the designation POLYCARBOPHIL by A. H. Robbins (Richmond, Va.). Other non-cytotoxic acrylic polymers suitable as pressure sensitive adhesives are known in the art and some of which are described in U.S. Pat. No. 3,645,835 to Hodgson, the relevant disclosure of which is incorporated by reference.

The spyrosorbent dressings of the present invention can further include medicaments or other active or diagnostic agents in the exudate transport layer which can be released or can contribute to maintaining a sterile microenvironment. These medicaments and like agents can be included, as desired, to be released for administration either continuously to exhaustion or in a controlled manner through selective dissolution, and can include wound healing agents, odor destroying agents, antiseptic agents, bacteriostatic agents, antimicrobial agents, wound debridement agents, moisture level indications, pain killing agents, pH indicators, and the like. Colorants and fillers can be included as well, if desired.

The spyrosorbent dressings are preferably low profile, self-supporting and conformable. However, supporting structures, such as mesh or filamentous scrim, can be included in the dressing architecture if desired or needed.

The following examples illustrate typical processes and compositions for practicing the present invention, but are not to be construed as limitations thereof.

EXAMPLE 1

Manufacture of Spyrosorbent Film Layer

A polymeric film layer was prepared from a segmented polyetherurethane-urea, sold under the trademark, MITRATHANE® (PolyMedica Industries, Inc., Golden, Colo.) as described below. The material was supplied as a 25 weight percent solids solution in dimethylacetamide (DMAC). Suitable materials of this type are described in U.S. Pat. No. 4,849,458 to Reed et al.

The solution was spread to the desired thickness on a glass plate and the solvent removed by heating to a temperature in the range of about 50° C. to about 70° C. for a period of about 2 hours. A series of films were prepared having a dry thickness in the range from of about 0.1 mil (about 0.25 microns) to about 20 mil (about 500 microns), preferably from about 0.1 mil to about 10 mils (about 250 microns), and more preferably from about 0.5 mil (about 12.5 microns) to about 2.5 mils (about 62.5 microns).

The physical and sorbent properties of the polymeric films produced having a thickness of about 1.3 to 1.5 mil (32.5 to 37.5 microns) were: tensile strength at break about 2.01±0.33 kg/mm²; elongation at break about 776±55%; wet MVTR of about 13,285±1839 g/m²/24 hrs; and dry MVTR about 3,807±151 g/m²/24 hrs. The calculated average ratio of wet to dry MVTR was about 3.5.

EXAMPLE 2

Manufacture of Adhesive Exudate Transport Layer

An adhesive exudate transport layer was prepared from a non-cytotoxic acrylic copolymer. Many pressure sensitive adhesives of this type are available commercially. A particularly useful adhesive sold under the trade name GELVA™ (Monsanto Chemical Co., St. Louis, Mo.) was employed. These adhesive materials are supplied as 40% solids solution in a solvent mixture.

The adhesive solution was printed onto a suitable release liner, e.g. siliconized paper, plastic film, etc., using a patterned gravure roller. A preferred pattern was that of a diamond shape with between about 20% and about 80% of the pattern being an open area. The release paper with its wet patterned adhesive print was placed in a forced hot air oven at a temperature of about 45° C. to about 75° C. for a period of about 2 hours to remove substantially all residual solvent. The final solvent-free material was a patterned pressure sensitive adhesive attached to a release liner.

EXAMPLE 3

Preparation of Spyrosorbent Film Wound Dressing with Adhesive Exudate Transport Layer A polymeric film layer was prepared as described in Example 1 having a thickness of about 1.5–2.0 mil±0.2 (about 37.5 to 50 microns). The film was then laminated together with the adhesive exudate transport layer prepared in Example 2 as follows. The lamination was performed by placing the film together with the patterned adhesive layer (supported by the release liner) such that the release liner face was away from the polymeric film face. Pressure was then applied to the composite structure to attain a bond between the polymeric film layer and the adhesive layer. The resulting laminate structure comprised the polymeric film attached to a patterned adhesive exudate transport layer. This laminate was further adhered to the release liner.

The release liner was removed, and the MVTR properties were determined. The typical sorbent properties of this type of film and adhesive spyrosorbent dressing indicated the following. Wet MVTR was about 7,057±411 g/m²/24 hrs and dry MVTR was about 2,507±117 g/m²/24 hrs. The calculated average MVTR ratio of wet to dry MVTR was about 2.8.

EXAMPLE 4

Preparation of Spyrosorbent Polymeric Wound Film Dressing With Gel Exudate Transport Layer A polymeric film was prepared as described in Example 1 to a thickness of about 1.5–2.0±0.2 mil (about 37.5 to 50 microns). To this film was laminated a gel material. Preferred materials comprise cross-linked polymeric matrices which contain between about 5% and about 99% (by weight) of water. For convenience, these are referred to as hydrogels. Preferably the hydrogel material exhibits some pressure sensitive adhesive properties.

Hydrogels of the type having utility in this invention can be obtained from a variety of commercial sources such as the material sold under the designation POLYHESIVE® sold by Valleylab, Inc., Boulder, Colo.; the designation PROMEON® hydrogel sold by Promeon, a division of Medtronic, Minneapolis, Minn.; and under the designation Hydrogel Pressure Sensitive Adhesive sold by the 3M Company, Minneapolis, Minn. Particularly preferred materials are those, sold under the trademark POLYHESIVE®, by Valleylab, Inc., Boulder, Colo.

Lamination of the polymeric film to the hydrogel was accomplished by placing the layers together and applying suitable pressure to attain the desired bond. This may be accomplished using nip rollers, or by applying weights to a platen placed on the laminate structure. The completed laminate comprised a polymeric film bonded to the hydrogel layer. The wound contacting surface of the hydrogel in turn was further adhered to a release liner removable for use.

Alternatively the hydrogel can be formed in situ on the polymeric film, thus removing the requirement for a subsequent lamination step in the process. The hydrogel film composite can then be further laminated to a suitable release liner.

Samples of this structure exhibited the following "intelligent" or differential MVTR properties: a wet MVTR of about 4,435±274 g/m²/24 hrs; a dry MVTR of about 2,876±69 g/m²/24 hrs and a water absorption capacity of about 271±8% of original weight after 3 hours immersion in distilled water. The calculated wet to dry MVTR ratio is about 1.5.

EXAMPLE 5

Preparation of Spyrosorbent Polymeric Film Wound Dressing With Foam Exudate Transport Layer A polymeric polyurethane film was prepared as described in Example 1 to a film thickness of about 1.5–2.0±0.2 mils (about 37.5 to 50 microns). To this polymeric film was laminated a layer of hydrophilic foam as described below. The preferred range of foam thickness was about 1/16 inch (about 0.17 cm) to about ½ inch (about 1.27 cm), and more preferably about 1/16 inch to about ¼ inch (about 0.64 cm). Useful hydrophilic foams of this type are sold under the name EPILOCK® by Calgon/Vestal Laboratories (St. Louis, Mo.), which is a polyurethane based material and foam manufactured from a chemical foaming system called HYPOL™ (W.R. Grace & Co.).

The polymeric film layer was laminated to the foam layer by applying heat at a temperature of from about 60° C. to about 120° C. and pressure of about 5 to about 20 pounds per square inch for a period of time of from about 10 minutes to about 1 hour.

Alternatively, the spyrosorbent polymeric film/adhesive laminate structure described in Example 3 can be further laminated to the foam by removing the release line and affixing the adhesive face onto the foam and applying pressure sufficient to attain the desired bond. The foam can cover all or a portion of the adhesive face to be present as an "island" on the film.

Wound dressings of the film and foam type (without the adhesive) exhibited the following differential MVTR sorbent properties; a wet MVTR of about 4,045±483 g/m²/24 hrs; a dry MVTR of about 2,120±103 g/m²/24 hrs and a water absorption capacity of about 208±64% of original weight after 3 hours immersion in water. The calculated average ratio of wet to dry MVTR was about 1.9.

EXAMPLE 6

Preparation of Spyrosorbent Polymeric Film Wound Dressing With Alginate Exudate Transport Layer A polymeric film/adhesive laminate was prepared as described in Example 3. The release liner was then removed.

To the adhesive layer of this structure, a fibrous mat of calcium alginate material was adhered by exerting a pressure on the alginate sufficient to activate the pressure sensitive adhesive properties of the underlying adhesive layer.

Calcium alginate materials are supplied as fibrous mats and are approximately 1/16 inch (about 0.17 cm) to about 1/2 inch (about 1.27 cm) in thickness. They are available in a variety of sizes. Useful alginates are commercially available under the Trademark SORBSAN® sold by Dow Hickam Pharmaceuticals, Inc., (Sugar Land, Tex.) and KALTOSTAT® sold by Calgon Vestal Laboratories (St. Louis, Mo.). Particularly preferred is KALTOSTAT®.

Preferably the alginate was positioned on the film/adhesive structure to form an "island". This provides for an adhesive border extending beyond the alginate layer affording a method of fixation of the dressing to the wound site. Alternately, the alginate can cover the entire adhesive surface. In such an embodiment, the resulting dressing requires a further securement means to affix it to the wound site.

Spyrosorbent wound dressings of this film-and-alginate composite exhibited the following differential MVTR properties: a wet MVTR of about $8,539\pm616$ $g/m^2/24$ hrs and a dry MVTR of about $2,307\pm81$ $g/m^2/24$ hrs. The calculated ratio of wet to dry MVTR was about 3.7.

EXAMPLE 7

Preparation of Spyrosorbent Polymeric Film Wound Dressing With Textile Exudate Transport Layer A polymeric film/adhesive laminate was prepared as described in Example 3. The release liner was then removed. To the adhesive layer was attached a textile material, such as gauze, or nonwoven textile, such as melt blown polypropylene, or nonwoven cotton containing blends by exerting pressure sufficient to activate the adhesive.

The textile material was medical grade gauze as supplied by Johnson & Johnson Co. Structures fabricated using gauze exhibited the following differential sorbent properties: a wet MVTR of about $14,515\pm1686$ $g/m^2/24$ hrs; a dry MVTR of about $2705\pm34$ $g/m^2/24$ hrs; and water absorption capacity of about $326\pm40\%$ of original after 3 hours immersion in water. The calculated ratio of wet to dry MVTR was about 5.4.

Dressings manufactured from melt blown polypropylene materials (Kimberly Clark, Roswell, Ga.) exhibited the following differential sorbent properties: a wet MVTR of about $7,799\pm750$ $g/m^2/24$ hrs and a dry MVTR of about $2,444\pm175$ $g/m^2/24$ hrs. The calculated ratio of wet to dry MVTR was about 3.2.

EXAMPLE 8

Preparation of Conventional Wound Dressings Having No Differential MVTR

This example illustrates a conventional laminate wound dressing structure which does not exhibit differential MVTR. The adhesive exudate transport layer described in Example 2 was prepared. To the adhesive surface of the adhesive/liner system was laminated a hydrocolloid mixture of hydroxymethylcellulose, pectin, gelatin, mineral oil, and rubber adhesive blend. This mixture is sold under the tradename STOMAHESIVE™ by Convatec/Squibb (Princeton, N.J.). The release liner was then removed and the MVTR of the laminate determined.

This laminated structure exhibited a fixed MVTR as shown by the following data: a wet MVTR of about $29\pm27$ $g/m^2/24$ hrs and a dry MVTR of about $29\pm27$ $g/m^2/24$ hrs. This calculates to a ratio of wet and dry MVTR of 1.

The laminated structures described above in each of Examples 3–7 can be cut into desired shapes and sizes and packaged into appropriate sized medical pouches. The packaged structure can be sterilized, preferably by gamma irradiation although steam or ethylene oxide sterilization techniques can be used. The sterile structure can then be used as a wound covering or dressing on a wide variety of dermal lesions and skin injuries.

EXAMPLE 9

Initiation of Moisture Vapor Transmission

Wound dressings of this invention and fabricated as described in Examples 1 and 3–7, above, were tested for their ability to initiate moisture vapor transmission. To that end, wound dressing samples about 3 inches in diameter were sealed against the open mouth of an upright aluminum cup that contained about 10 to 20 milliliters of water. These sample bearing cups were then placed on a laboratory bench and kept there at ambient temperature (about 20–25° C.). A glass sheet having a moisture sensitive paste on one face of the sheet was placed over each sample bearing cup with the moisture sensitive paste contiguous with the sample. The moisture sensitive paste was SAR-GEL, commercially available from Sartomer Company, Exton, Pa., U.S.A. This particular moisture sensitive paste undergoes a color change from "white" to "red-purple" when exposed to water.

Each dressing sample was tested in triplicate. The time period for a color change from "white" to "red-purple" was noted for each sample, the noted values were recorded, and an average value was determined for each sample group. The control, run concurrently, was a glass sheet with the same moisture sensitive paste kept at ambient conditions in the laboratory. The results are presented in Table I, below.

TABLE I

Spyrosorbent Wound Dressings for Exudate Management

| Dressing Description | Average Elapsed Time to Initiate Moisture Vapor Transmission (Minutes) | Example # |
| --- | --- | --- |
| Thin Film | $21\pm4$ | #1 |
| Thin Film & Adhesive | $33\pm4$ | #3 |
| Thin Film/Gauze | $32\pm7$ | #7 |
| Thin Film/Melt blown non-woven | $39\pm3$ | #7 |
| Thin Film/Alginate | $53\pm8$ | #6 |
| Thin Film/Foam | $63\pm4$ | #5 |
| Thin Film/Hydrogel | $131\pm6$ | #4 |
| Control[1] | >540 | — |

[1]The control was the moisture sensitive paste applied to a glass plate and exposed to ambient laboratory atmosphere.

The foregoing results indicate that the dressing of the present invention exhibiting the longest time period for onset of moisture vapor transmission ("breathing") was the hydrogel/hydrophilic film laminate and the dressing of the present invention exhibiting the shortest time period was the hydrophilic film above. These results demonstrate that the time period to initiate "breathing" by the present wound dressings can be suitably adjusted and modulated by the selection of one or more hydrophilic exudate transport layers to meet specific wound exudate management requirements. The moisture vapor transmission lag time preferably is in the range of about 30 minutes to about 150 minutes.

The foregoing Examples and the accompanying discussion are intended to be illustrative and are not to be taken as limiting. Still other variations within the spirit and scope of this invention are possible and will readily present themselves to those skilled in the art.

We claim:

1. A sheet-form composite suitable as a spyrosorbent wound dressing which comprises: (a) a monolithic, hydrophilic film layer characterized by having a moisture vapor transport rate of greater than about 2,600 g/m$^2$/24 hrs when dry and a wet to dry moisture vapor transport rate ratio greater than 1 and (b) a hydrophilic and absorptive exudate transport layer contiguous with at least a portion of the film layer, the exudate transport layer providing a wound contacting face for the sheet-form composite, the moisture vapor transport rate of the composite being greater than 2,000 g/m$^2$/24 hrs when dry, and greater than about 3,000 g/m$^2$/24 hrs when wet.

2. The sheet-form composite of claim 1 further including a pressure sensitive adhesive layer on at least a portion of the wound contacting side of the sheet-form composite.

3. The sheet-form composite of claim 1 wherein the wet to dry moisture vapor transport rate ratio of the sheet-form composite is in the range of about 1.5 to about 10.

4. The sheet-form composite of claim 1 wherein the wet to dry moisture transport rate ratio of the sheet-form composite is in the range of about 2.5 to about 5.5.

5. The sheet-form composite of claim 1 wherein the film layer is a segmented polyetherurethane urea resin.

6. The sheet-form composite of claim 1 wherein the film layer has a thickness of less than about 5 mils (about 125 microns) when dry.

7. The sheet-form composite of claim 1 wherein the film layer has a thickness of about 1 mil (about 25 microns) to about 1.5 mils (about 37.5 microns) when dry.

8. The sheet-form composite of claim 1 where the exudate transport layer is selected from the group consisting of a hydrocolloid, a gel, a foam, a membrane, a textile, an adhesive and combinations thereof.

9. The sheet-form composite of claim 1 wherein the exudate transport layer comprises a hydrophilic pressure sensitive adhesive applied to at least a portion of the film layer in a discontinuous pattern.

10. The sheet-form composite of claim 1 wherein the film layer is a segmented polyurethane-urea polymer and the exudate transport layer is a hydrocolloid.

11. The sheet-form composite of claim 1 wherein the film layer is a segmented polyurethane-urea polymer and the exudate transport layer is a gel containing, on a weight percent basis of the gel, about 1% to about 99% water.

12. The sheet-form composite of claim 1 wherein the film layer is a segmented polyurethane-urea polymer and the exudate transport layer is a foam.

13. The sheet-form composite of claim 1 wherein the film layer is a segmented polyurethane-urea polymer and the exudate transport layer is a textile selected from the group consisting of a woven textile, a nonwoven textile, and combinations thereof.

14. The sheet-form composite of claim 1 wherein the film layer is a segmented polyurethane-urea polymer and the exudate transport layer is a polyurethane-based membrane having a controlled pore size.

15. The sheet-form composite of claim 1 further including medicaments in the exudate transport layer.

16. The sheet-form composite of claim 1 contained in a sterile package.

17. The sheet-form composite of claim 1 wherein the wound contacting face of the exudate transport layer is adhesive.

18. The sheet-form composite of claim 1 further including a releasable liner applied to the adhesive.

19. The sheet-form composite of claim 1 wherein moisture vapor transmission from said composite is initiated after a lag time in the range of about 30 minutes to about 150 minutes.

20. A method of protecting a wound which comprises applying the spyrosorbent dressing of claim 1 to said wound.

* * * * *